US010046148B2

(12) United States Patent
Griffith

(10) Patent No.: US 10,046,148 B2
(45) Date of Patent: Aug. 14, 2018

(54) TISSUE BONDING IMPLANTATION DEVICE AND METHOD

(71) Applicant: Donald Griffith, Houston, TX (US)

(72) Inventor: Donald Griffith, Houston, TX (US)

(*) Notice: Subject to any disclaimer, the term of this patent is extended or adjusted under 35 U.S.C. 154(b) by 332 days.

(21) Appl. No.: 14/648,073

(22) PCT Filed: Nov. 27, 2013

(86) PCT No.: PCT/US2013/072304
§ 371 (c)(1),
(2) Date: May 28, 2015

(87) PCT Pub. No.: WO2014/085634
PCT Pub. Date: Jun. 5, 2014

(65) Prior Publication Data
US 2015/0314112 A1    Nov. 5, 2015

Related U.S. Application Data

(60) Provisional application No. 61/731,532, filed on Nov. 30, 2012.

(51) Int. Cl.
*A61M 27/00*  (2006.01)
*A61M 25/02*  (2006.01)
*A61M 25/04*  (2006.01)
*A61M 25/00*  (2006.01)

(52) U.S. Cl.
CPC ......... *A61M 27/00* (2013.01); *A61M 25/0017* (2013.01); *A61M 25/02* (2013.01); *A61M 25/04* (2013.01); *A61M 2025/0056* (2013.01); *A61M 2025/0233* (2013.01); *A61M 2025/0293* (2013.01)

(58) Field of Classification Search
CPC ...... A61M 2025/0293; A61M 25/0017; A61M 25/02; A61M 25/04
See application file for complete search history.

(56) References Cited

U.S. PATENT DOCUMENTS

| | | | |
|---|---|---|---|
| 4,932,938 A | 6/1990 | Goldberg et al. |
| 5,234,408 A | 8/1993 | Griffith |
| 5,707,357 A | 1/1998 | Mikhail et al. |
| 5,766,249 A | 6/1998 | Griffith |
| 6,254,570 B1 | 7/2001 | Rutner et al. |
| 6,663,589 B1 | 12/2003 | Halevy |
| 2004/0243064 A1 | 12/2004 | Sommerich |
| 2005/0251174 A1 | 11/2005 | Gill et al. |
| 2012/0136324 A1 | 5/2012 | Hanuka et al. |

*Primary Examiner* — Tatyana Zalukaeva
*Assistant Examiner* — Kai Weng
(74) *Attorney, Agent, or Firm* — The Law Firm of H. Dale Langley, Jr., P.C.

(57) ABSTRACT

A tissue bonding implantation device includes an internal drainage tube having an internal surface and an external surface, an inflatable balloon in the shape of a toroid encircling the outer surface of the internal drainage tube, and a balloon inflation conduit in fluid communication with an interior of the inflatable balloon. A transcutaneous sleeve in the form of a tube having an internal diameter allows the sleeve to fit over the external surface of the internal drainage tube, and the sleeve includes a horizontal flange positioned at a top edge of the sleeve.

9 Claims, 8 Drawing Sheets

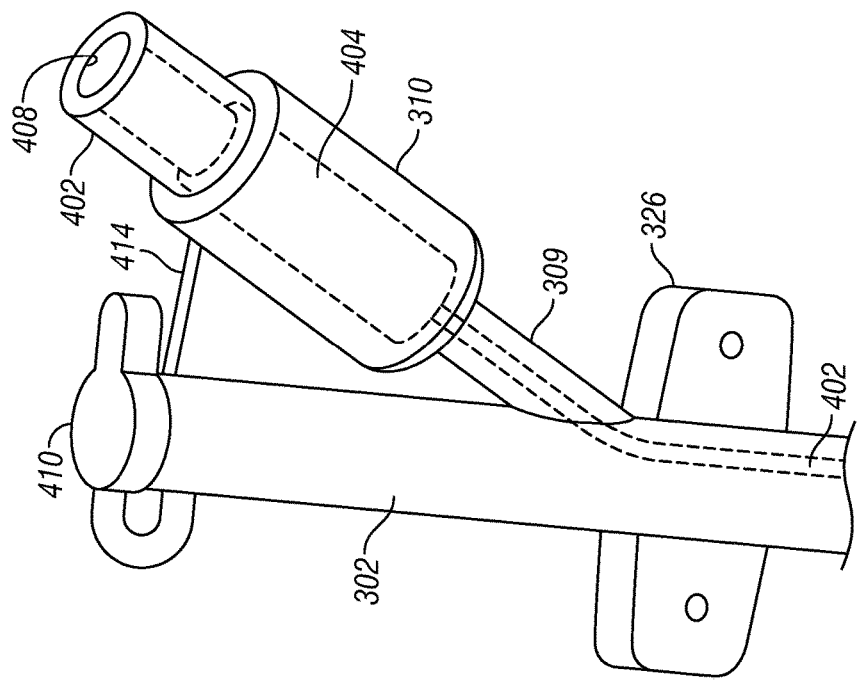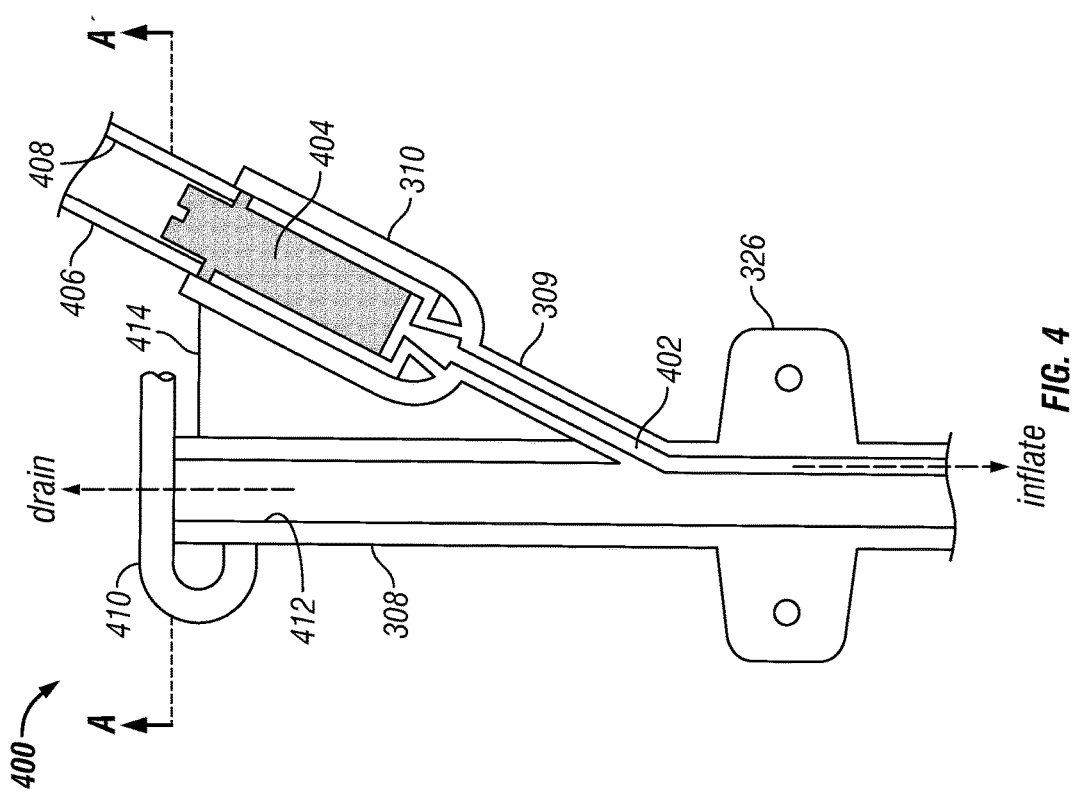

TISSUE BONDING IMPLANTATION DEVICE AND METHOD

CROSS-REFERENCE TO RELATED APPLICATION

The present application is a conversion of and has benefit of priority of the following application, which has at least one same inventor of the present application: U.S. Provisional Patent Application No. 61/731,532, titled "A Tissue Bonding Implantation Device", filed Nov. 30, 2012.

TECHNICAL FIELD

The present invention generally relates to cystostomy catheters, and more particularly relates to tissue bonding implantation devices and methods for fluid drainage.

BACKGROUND

Clinical applications of transcutaneous catheters include, for example, suprapubic bladder drainage, transcutaneous and intrathoracic access to central venous vessels, peritoneal dialysis, and intravascular access for chemotherapy, among others. Use of transcutaneous catheters in these treatments permit skin microbes to adhere to catheter surfaces to migrate along the catheter. The microbes then may enter the body by adhering, replicating and migrating within biofilms into intra-corporeal organs.

In the case of suprapubic bladder drainage, in particular, the urinary bladder is a hollow spherical muscle that serves as a muscular reservoir to hold about 8-12 ounces of urine. A sphincter muscle at the bladder outlet normally closes around the urethra to allow the bladder to fill with and retain urine. During filling, the bladder is relaxed and the sphincter muscle is contracted. The nervous system normally alerts the brain when the bladder is near full, triggering an urge to expel the urine contents of the bladder. During normal urination, the brain triggers pelvic nerves that cause the bladder muscle to contract and the sphincter muscle to relax in coordinated manner. Urine is then expelled from the bladder through the urethra.

Neurological damage, and other maladies, can impair contraction and coordination of the bladder and sphincter muscles. Loss of bladder control can result in incontinence. Spinal cord injury (SCI) is a non-exclusive example instance in which neurological damage may disrupt or impair normal operation of the urinary bladder. Most SCI patients can have chronic urinary retention. Some have incontinence and/or a combination of chronic retention with episodic incontinence. A high percentage of SCI patients use intermittent catheterization, Foley urethral catheter drainage, and/or suprapubic bladder drainage methods to evacuate the bladder on a chronic basis.

Foley and suprapubic bladder drainage are open access, meaning that skin microbes have constant access to external surfaces of these chronic, indwelling, drainage tubes Skin microbes adhere to external catheter surfaces. As microbes replicate, they migrate (mostly) along the exterior catheter surfaces and thereby gain access to the bladder lumen. The external catheter surface is constantly moistened with urine or urethral mucous or both. About 100% of SCI patients utilizing Foley urethral or suprapubic tube drainage for (on the order of) about >60 days have microbial colonized urine. Existing antimicrobial-coated tubes or systemic antibiotics can reduce the colonization rate, for example, from approximately 5%/day to approximately 2-3%/day. This prophylactic use of antimicrobial agents invites colonization by antibiotic resistant microbes.

Bacteria have two life-styles, planktonic (i.e., floating) or sessile (i.e., attached to a surface). Urinary pathogens typically have sugar molecules on their surface causing them to adhere to catheter surfaces where they may multiply rapidly. Concentrations of adherent microbes may frequently exceed on the order of about 106/ml in 24 hours and 107/ml in 48 hours. Microbial metabolism changes in these sessile, dense microbial colonies. This phenomenon is called quorum signaling. Quorum signaling creates microbial biofilms which are slimy mixtures of peptides, amino acids, proteoglycans, and cellular and microbial debris. The biofilm acts as a sanctuary. Microbes trapped within the biofilm may be, for example, on the order of about 1000×-10,000× more resistant to traditional antibiotics than are planktonic microbes.

Thus, SCI patients and others that utilize traditional, chronic, indwelling Foley urethral catheters and suprapubic tubes are subject to constant access of skin microbes to external surfaces of urethral catheters. Resident skin microbes adhere, multiply explosively, and migrate as dense colonies along the catheters primarily on the external surface into the bladder lumen. These migrating bacteria form biofilms on catheter surfaces that harbor and perpetuate microbial growth and increase resistance to antimicrobial agents. Antibiotics can sterilize urine by killing planktonic bacteria but have little or no effect on biofilm embedded organisms on the catheter surfaces. Thus, continuous access of skin microbes to catheter surfaces cause Catheter-Associated Urinary Tract Infection [CAUTI] which is widely recognized as a major chronic problem increasing morbidity rates.

It would therefore be desirable, and a significant improvement in the art and technology, to provide systems, devices and methods for transcutaneous catheter treatment, including for bladder drainage, on a long term basis, which systems, devices and methods prevent or reduce bacterial incursion, adhesion, and/or formation of biofilms.

SUMMARY

An embodiment of the invention is a tissue bonding implantation device including an internal drainage tube having an internal surface and an external surface, an inflatable balloon in the shape of a toroid encircling the outer surface of the internal drainage tube, a balloon inflation conduit in fluid communication with an interior of the inflatable balloon, a transcutaneous sleeve in the form of a tube having an internal diameter allowing the sleeve to fit over the external surface of the internal drainage tube, and a cap positioned at a top edge of the sleeve or more distally in the internal drainage tube. The external cap has a first sealable opening in fluid communication with the drainage tube and a second sealable opening in fluid communication with the balloon inflation conduit, the balloon inflation conduit extending from the balloon to the cap proximate to the sleeve, and a reversible tissue-bonded anchor that is reversibly attached onto the outer surface of the drainage tube. Inflation of the balloon on the internal drainage tube reversibly engages and secures the drainage tube in a water-tight manner within the anchor.

Another embodiment of the invention is a tissue bonding implantation device including a drainage tube having an internal surface and an external surface, an inflatable balloon connected to the drainage tube, on the external surface of the drainage tube, a balloon inflation conduit in fluid communication with the inflatable balloon, the balloon inflation conduit extends through the drainage tube from the inflatable balloon, to an external cap connected to the drainage tube and the balloon inflation conduit, the cap having a first sealable opening in fluid communication with the drainage tube and a second sealable opening in fluid communication with the balloon inflation conduit, and an anchor forming an inflation void, the inflatable balloon expands via injection through the external cap and balloon inflation conduit. Fluid injection via the external cap fills the balloon within the inflation void of the anchor, to retain the drainage tube with the anchor.

Yet another embodiment of the invention is a catheter for connection to a vessel. The catheter includes an anchor connected to the vessel, the anchor includes a first lock device, and a drain tube, the drain tube includes a second lock device for reversibly and sealingly mating with the first lock device.

Another embodiment of the invention is a method of tissue bonding for a catheter. The method includes implanting an anchor to a drain vessel, guiding a drain tube through the anchor, and locking the drain tube to the anchor.

BRIEF DESCRIPTION OF THE DRAWINGS

The present invention is illustrated by way of example and not limitation in the accompanying figures, in which like references indicate similar elements, and in which:

FIG. 4 illustrates a partial side view in cross-section along line A-A' of FIG. 3 of an exemplary dual channel cap, according to certain embodiments of the invention;

FIG. 5 illustrates a partial side perspective view of the exemplary dual channel cap of FIG. 4, according to certain embodiments of the invention;

DETAILED DESCRIPTION

A non-exclusive embodiment according to the present invention of a tissue bonding implantation device includes an internal drainage tube having an internal surface and an external surface, an inflatable balloon in the shape of a toroid encircling the outer surface of the internal drainage tube, a balloon inflation conduit in fluid communication with an interior of the inflatable balloon, a transcutaneous sleeve in the form of a tube having an internal diameter allowing the sleeve to fit over the external surface of the internal drainage tube, and an external cap that is variably positioned at a severed end of the internal drainage tube or at the distil end of the internal drainage tube, the cap has a first sealable opening in fluid communication with the drainage tube and a second sealable opening in fluid communication with the balloon inflation conduit, the balloon inflation conduit extending from the balloon to the cap proximate to the sleeve, and a tissue-bonding anchor that bonds in a water-tight manner to the internal drainage tube when the balloon on the internal drainage tube is inflated with air or a fluid such as water or saline.

Figure 1:
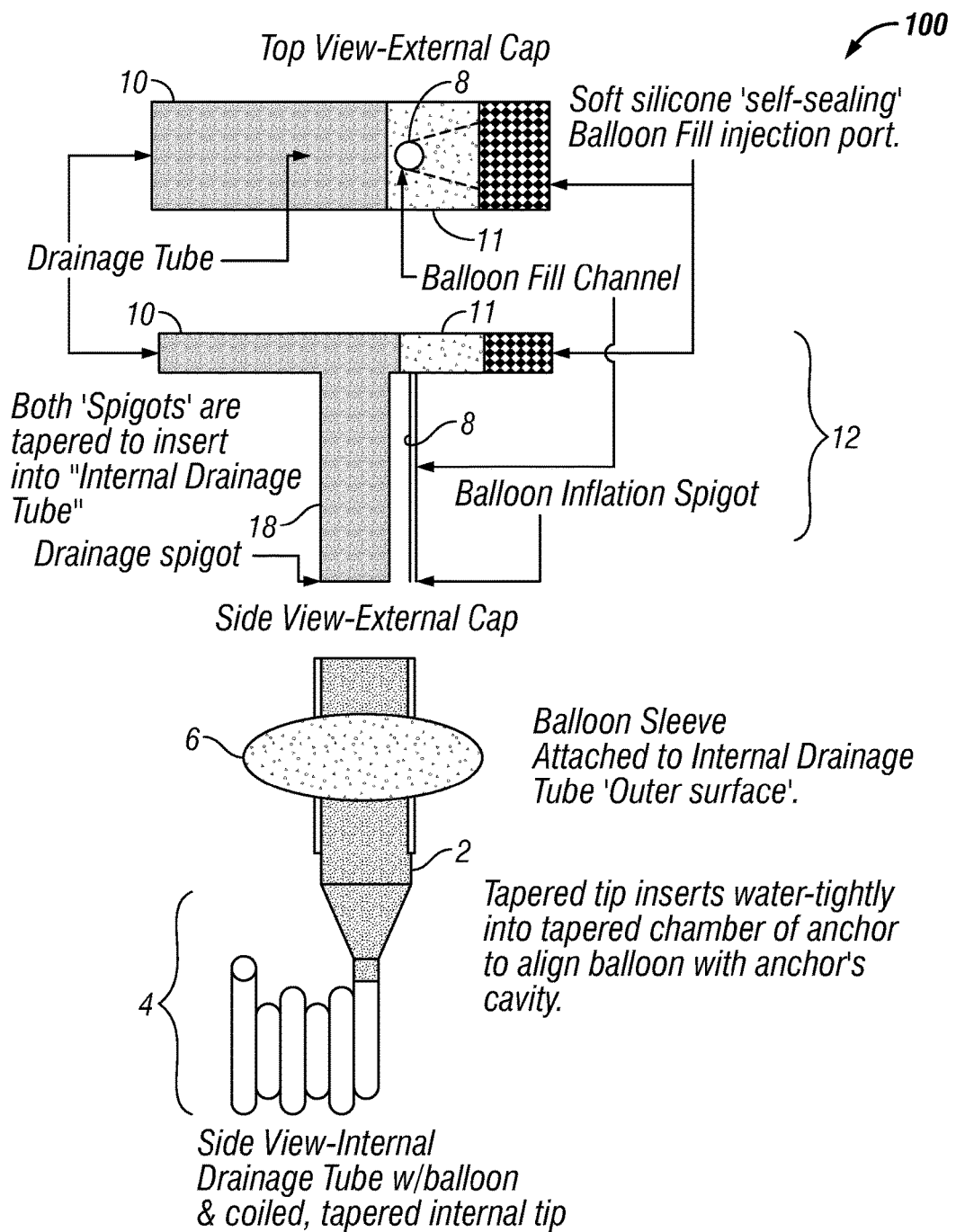
FIG. 1 illustrates an exploded view of an example of a tissue bonding implantation device, according to certain embodiments of the invention.

Referring to FIG. 1, a non-exclusive example embodiment of a tissue bonding device 100 includes an internal drainage tube 2. The internal drainage tube 2 is hollow. A bottom portion 4 of the drainage tube 2 may, but need not necessarily, be inwardly tapered. Although illustrated as a tube having a generally cylindrical cross sectional shape in FIG. 1, the drainage tube 2 may have any acceptable cross sectional shape provided a transcutaneous sleeve 314 (not shown in FIG. 1, but later described and shown in FIGS. 3, 8 and 9) is appropriately shaped to match that of the drainage tube 2. The drainage tube 2 is designed to be implanted internally in a body such that an opening (or series of openings, as applicable) on the lower end of the drainage tube 2 is in fluid communication with a fluid to be removed from or injected into a body.

An inflatable balloon 6, for example, generally in the shape of a toroid or otherwise, surrounds an outside surface of the drainage tube 2. An interior of the inflatable balloon 6 is in fluid communication with a balloon inflation conduit 8. The balloon inflation conduit 8 extends from the balloon 6 to a cap 12 and permits the introduction and release of fluids into the inflatable balloon 6. Such fluids may include, by way of example, water, saline and air.

In certain embodiments, the transcutaneous sleeve 314 (shown in FIGS. 3, 8 and 9) is a hollow tube designed to fit around the internal drainage tube 2 and to lie beneath the skin within subcutaneous fat. In one embodiment, the transcutaneous sleeve 314 has a flange 330 (shown in FIGS. 3, 8 and 9) connected to an upper edge of the sleeve such that the flange sits on the skin surface.

As shown in FIG. 1, the removable external cap 12 is configured to seal a top opening 18 of the drainage tube 2 and a top opening 11 of the balloon inflation conduit 8. The cap 12 may be attached to the end of the internal drainage tube 2 or at any point where the internal drainage tube 2 may be severed during insertion, for example, typically the internal drainage tube 2 is severed flush with the skin surface. The external cap 12 is designed to insert into both channels (i.e., the balloon inflation conduit 8 and the drainage channel of the drainage tube 2, itself) of the internal drainage tube in a watertight friction-fit manner.

Figure 2:
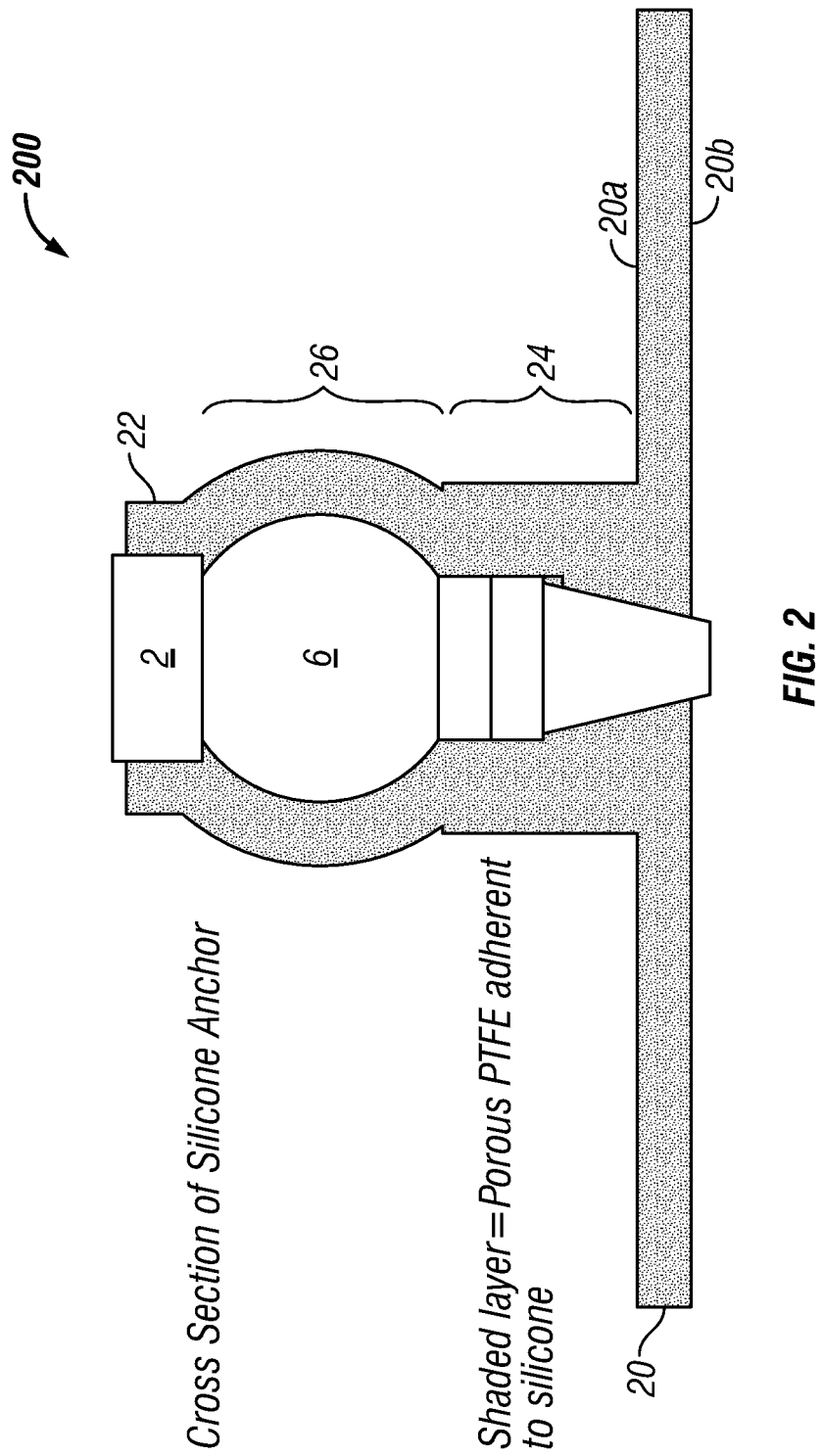
FIG. 2 illustrates a sectional elevational view of an example of a tissue bonding anchor as positioned on a bottom portion of a drainage tube and balloon, according to certain embodiments of the invention.

Referring to FIG. 2, an embodiment of a tissue-bonding anchor 200 is shown in cross section. The tissue-bonding anchor 200 becomes bonded in a water-tight and reversible manner to the internal drainage tube 2 when the balloon 6 on the internal drainage tube 2 is inflated with a fluid, gas, or air (i.e., within an expanded balloon chamber 26, as hereafter described). The anchor 200 includes, for example, a silicone flange 20 (oriented horizontally in FIG. 2) and a silicone cylinder 22 (oriented vertically in FIG. 2). The top and bottom external surfaces 20a, 20b, respectively, of the flange 20 and a portion of the cylinder 22 are coated with a porous polymer such as polytetrafluoroethylene (PTFE, e.g., Teflon™) or polyester (e.g., Dacron). Only the cylindrical segment 24 adjacent to the silicone flange 20 is coated with porous polymer; this partial coating is designed to keep the porous polymer below the recuts abdominis fascia and within the rectus abdominis muscle. The anchor 200 contains an expanded chamber 26 within the cylindrical segment 24 that is designed to accept the inflated balloon 6 in a secure and water-tight manner. The anchor 200 is designed to be permanently implanted into the body by, for example, suturing or other suitable bonding. The anchor 200 may be attached extra-peritoneally, such that the internal drainage tube 2 is in fluid communication with the desired body component, for example, the urinary bladder. Ideally, the anchor can be, for example, inserted into potential space surgically developed within the body wall bounded anteriorly by the rectus abdominis muscle and posteriorly by the transversalis fascia.

The remainder of the components are preferably made of silicone. The transcutaneous sleeve 318 (shown in FIGS. 3, 8 and 9) is preferably impregnated or coated with antimicrobial agents. The antimicrobial molecules may be elutable or non-elutable bonded to the external surface of the sleeve. Antimicrobial quantities, such as are known in the art, such as biofilm dispersants, quorum signaling inhibitors, slick surface molecules, anti-fungals, bacteriostatic agents and bactericidal agents may be used. Therapeutic concentrations of these agents may elute or not elute, as desired in the application, so as to deliver their therapeutic effect to microbes, fungi, and viruses that seek to attach and replicate on the device surfaces. Certain materials of construction for the various components of the tissue bonding device include, for example, the tissue-bonding anchor 200 is made of silicone, polyurethane, or other synthetic polymer or metal with an outer layer of porous polymer, such as, for example, polytetrafluoroethylene (PTFE) or polyester, on all or a portion of the anchor 200. The anchor 200 may be of varied shape, for example, as a three-dimensional ellipsoid with a smooth external surface externally, having the expanded chamber 26 for the balloon being totally contained within the 3-D ellipsoid, or other suitable or desired configuration.

Figure 3:
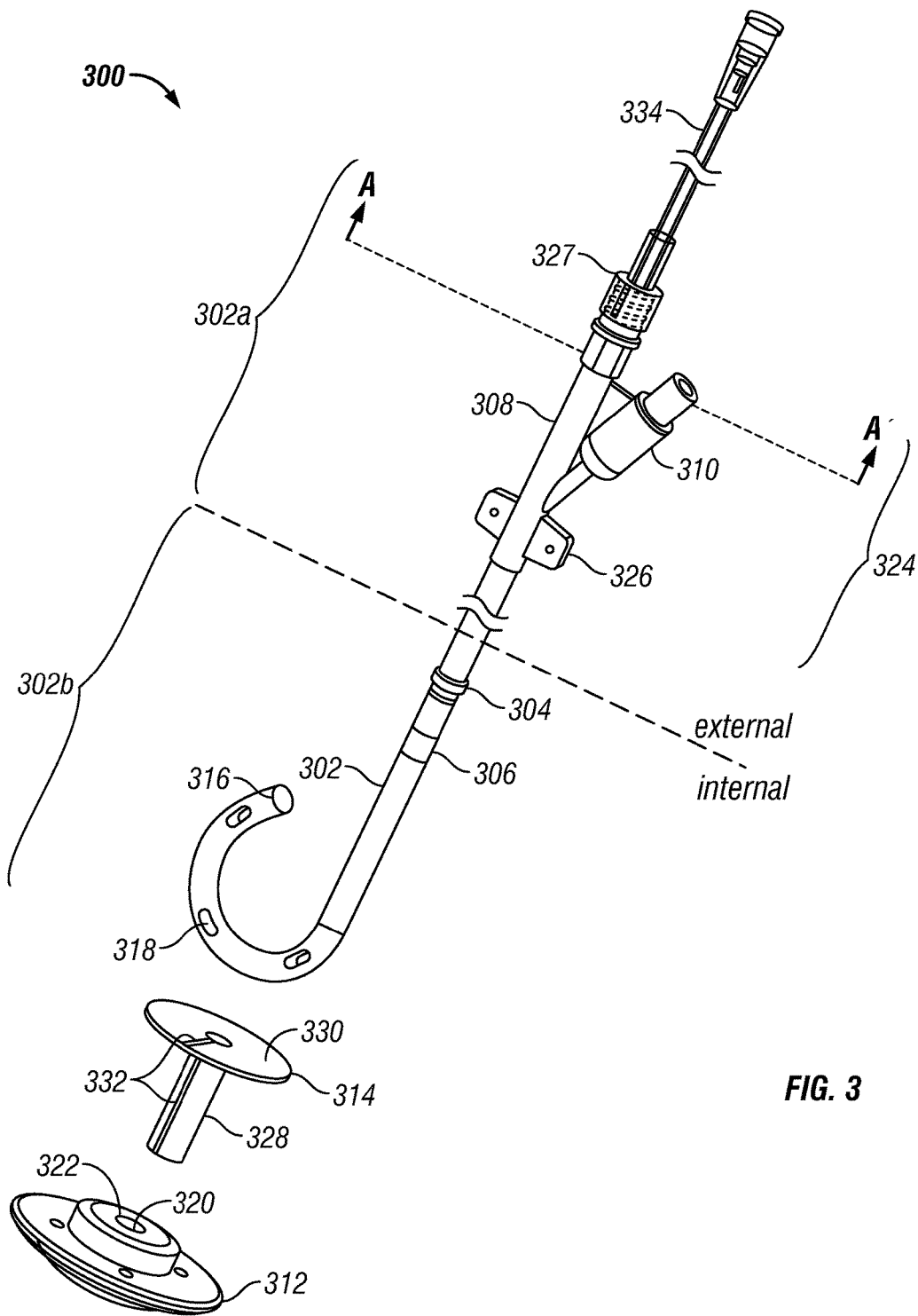
FIG. 3 illustrates a side perspective view of an exemplary bonding implantation device, according to certain embodiments of the invention.

Referring to FIG. 3, a non-exclusive embodiment of a tissue bonding implantation device 300 includes a drainage tube 302. The drainage tube is hollow and may be cylindrical or have other suitable cross sectional shape for extending into a human body via an opening of the body, such as a cystostomy or other body opening. The drainage tube 302 includes an external portion 302a and an internal portion 302b. In use, the external portion 302a extends external to a mammalian body from a cystostomy or other body opening, and the internal portion 302b of the drainage tube 302 extends into and through the cystostomy or other body opening to access, fill, or drain a region, cavity or space such as within the urinary bladder or some other organ, space or potential space. In this manner the drainage tube passes transcutaneously into the mammalian body, with the external portion 302a residing external to the body and the internal portion 302b extending in the body into the drain region. In FIG. 3, the external components 302a are permanently attached to the internal drainage tube 302b. External components 302a may be used as illustrated. Alternatively, tube 302 can be severed above a distal or bottom end (at 304 in FIG. 3), commonly at the skin surface, for example, and the removable external cap 10 (shown in FIG. 1) or similar element(s) may be substituted for components 302a.

The internal portion 302b of the drainage tube 302 extends to a bottom end 316. A settlement ring 304 is fixed to and encircles the exterior cross section of the drainage tube 302 a distance from the bottom end 316. The internal portion 302b, from the settlement ring 304 to the bottom end 316, is sized to fit within the drain region, for example, within the urinary bladder or other drain region, and to allow adequate drainage from the drain region. Towards the bottom end 316 along the drainage tube 302, the drainage tube 302 is formed with holes 318 through the wall of the tube 302. The holes 318 allow fluids of the drain region to flow from outside the tube 302, through the wall of the tube 302, and within the hollow of the tube 302. Or, alternatively, if the drainage tube 302 is employed for delivery of fluids, the fluids pass within the hollow of the tube 302, through the holes 318 of the wall of the tube 302, and outside the tube 302 in vicinity of the holes 318.

An anchor 312 of the tissue bonding catheter implantation device 300 includes a central cylinder 319 forming a central channel 320 through the anchor 312. The central channel 320 is sized to accommodate the bottom end 316 extending into and through the central channel 320 of the central cylinder 319. An accommodation seat 322 at an upper end (in the orientation of FIG. 1) of the central channel 320 is sized to mate with the settlement ring 304 upon passage of the bottom end 316 into the upper end (in the orientation of FIG. 1) of and through the central channel 320. The internal drainage tube 302 may be tapered so that it inserts snugly and in a watertight manner with the bottom aperture of the central channel 320 concurrently with the mating of the accommodation seat 322 and settlement ring 304.

An inflatable balloon 306 is fixed externally to the drainage tube 302 below (in the orientation of FIG. 3) the settlement ring 304. The inflatable balloon 306 is, for example, toroidal in shape and encircles the drainage tube 302 in connection thereto. Although not shown in detail in FIG. 3, the anchor 312 is formed with an internal balloon inflation void 608 (shown in FIGS. 6 and 8) along the central channel 320. The internal balloon inflation void 608 is sized to accommodate the inflatable balloon 306 when inflated, with the bottom end 316 extending into the upper end (in the orientation of FIG. 1) of the central cylinder 319 through the central channel 320, such that the settlement ring 304 rests in the accommodation seat 322.

Continuing to refer to FIG. 3, the external portion 302a of the drainage tube 302 is sized to extend externally from the body when the internal portion 302b resides in the body. A permanently attached terminal end (upper end in the orientation of FIG. 3, with details shown in FIGS. 4 and 5) of the external portion 302a is connected to or forms a dual-channeled cap 324. A first channel 308 of the dual-channeled cap 324 extends the drainage tube 302 to form a channel for connection to a drain conduit 334. The drainage tube 302 provides a channel for flow of fluids into the tube 302 from a region, through the tube 302, and passing to and through the first channel 308 of the cap 324. In this manner, the drainage tube 302 and first channel 308 provide a conduit for drainage of a fluid, for example, urine (or other fluid, as applicable), from a drainage region, for example, the bladder (or other region, as applicable). A connector 327 at an upper end (in the orientation of FIG. 1) of the first channel 308 may be connected to a drain tube 334 or similar conduit, for example, the drain tube 334 connects to a collection bag or collection reservoir for drained fluids.

Continuing to refer to FIG. 3, (with reference to FIG. 4), a second channel 309 of the dual-channeled cap 324 forms a valved external inflation conduit 310. The external inflation conduit 310 connects through the first channel 308 to an internal inflation conduit 402 (not shown in detail in FIG. 3, but shown in FIGS. 4, 5 and 8). The internal inflation conduit 402 passes within the drainage tube 302 and connects to the inflatable balloon 306. The inflatable balloon 306 is inflatable via the valved external inflation conduit 310 and the internal inflation conduit 402. A source (not shown in detail) of a pressurized fluid, such as saline, air or other gas or liquid, is connected to the valved external inflation conduit 310 to admit the pressurized fluid into the internal inflation conduit 402 and on to the inflatable balloon 306.

The dual-channeled cap 324 may also include wing tabs 326 or other extensions to assist handling and management of the external portion 302a of the drainage tube 302. For example, the wing tabs 326 provide surface for taping or securement of the external portion 302a to the external skin of the body or otherwise. Although not shown in FIG. 3 (but shown as a non-exclusive example, in FIGS. 4 and 5), one or more plug or cap may provide sealed containment of fluids by the dual-channeled cap 324.

A transcutaneous sleeve 314 of the tissue bonding catheter implantation device 300 includes a hollow transcutaneous extension 328 connected to a disk flange 330. The transcutaneous extension 328 and the disk flange 330 include a slit 332. Via the slit 332, the transcutaneous sleeve 314 is flexed to enlarge the opening of the slit 332 to accept the drainage tube 302 in the transcutaneous extension 328, in vicinity of the intersection of the internal portion 302b and external portion 302b, such that the drainage tube 302 extends within the hollow transcutaneous extension 328. In use with the body and the drainage tube 302, the transcutaneous extension 328 is placed at the cystostomy or other body opening and inserted to extend through the skin of the body, until the disk flange 330 rests on the skin. In this manner, the transcutaneous sleeve 314 shields the drainage tube 302 from contact with the skin and cutaneous layers. The transcutaneous sleeve 314, via the slit 332, may be replaced by flexing the sleeve 314 to open the slit 332 and remove the sleeve 314 from around the drainage tube 302, and providing a next sleeve 314 to the tube 302, to avoid microbe contamination of the drainage tube 302 from the skin and subcutaneous layers. The transcutaneous sleeve 314 also serves to fill the potential void space above the settlement ring 304 (shown in FIGS. 3 and 8).

In operation, the anchor 312 is surgically affixed, such as by sutures or other bond, to a wall of an organ, space or potential cavity such as a muscular or other reservoir within a mammalian body (for example, the wall of the bladder if the tissue bonding catheter implantation device 300 is employed for bladder urine drainage). The internal portion 302b of the drainage tube 302 is fed, via a cystostomy opening or otherwise, through the central channel 320 of the anchor 312, until the settlement ring 304 mates with the accommodation seat 322. In this manner, the bottom end 316 of the drainage tube 302 resides in the preferred access location or drain vessel, such as the bladder, to allow drainage from the drain vessel through the holes 318 and in the drainage tube 302.

Upon mating of the settlement ring 304 to the accommodation seat 322, the inflatable balloon 306 is positioned to be inflated, via the valved external inflation conduit 310 forming the second channel 309 and through the internal inflation conduit 402. The inflatable balloon 306 is inflated sufficiently to inflate the internal balloon within the inflation void 608 (not shown in FIG. 4, but shown in FIGS. 6 and 8) of the anchor 312. The inflatable balloon 306, as so inflated, forms a fluid impermeable seal with the anchor 312. The inflatable balloon 306, as so inflated, also retains the drainage tube 302 in engagement to the anchor 312 and extending into the drain vessel, such as the bladder. The drain vessel, such as the bladder, then drains through the drainage tube 302 and through the first channel 308.

The first channel 308 may be connected by the connector 327 to a collection bag, such as a urine collection bag or tube to such bag or another collector. The transcutaneous sleeve 314 may be placed, and replaced, in engagement with the drainage tube 302 at a cystostomy or other body opening, to shield the tissue bonding catheter implantation device 300 from contact with the skin and transcutaneous layers of the body adjacent the drainage tube 302. The drainage tube 302 may be inserted over a guide wire (not shown) through the cystostomy and central channel 320 of the anchor 312, such that the bottom end 316 extends through the drainage reservoir (e.g., bladder) wall and into the reservoir (e.g., in the bladder). The balloon 306 is inflated to seal the tube 302 to the anchor 312. The drainage tube 302 may be removed upon deflation of the balloon 306, and then replaced through same procedure to again seal against the anchor 312.

Referring to FIGS. 4 and 5, in conjunction with FIG. 3, a non-exclusive embodiment 400 of the dual-channel cap 324, shown in cross-section taken along line A-A' of FIG. 1, includes the internal inflation conduit 402. The internal inflation conduit 402 extends from the valved external inflation conduit 310, to the internal balloon inflation void 608 (not shown in FIG. 4, but shown in FIGS. 6 and 8), within the hollow drainage tube 302 (shown in FIGS. 3 and 8). The valved external inflation conduit 310 contains a valve 404. The valved external inflation conduit 310 connects to an inflation inlet 406. The inflation inlet 406 is hollow 408 and sized to mate with a source of pressurized fluid, for example, saline, other liquid, air or gas (not shown in FIG. 4). The valve 404 allows pressurized fluid or gas of the source to be passed via the hollow 408 into the internal inflation conduit 402 to inflate the inflatable balloon 306 (shown in FIGS. 3 and 8), when the source is connected to the inflation inlet 406. The valve 404 prevents escape of the pressurized fluid or gas, and thus the inflatable balloon 306 remains inflated, unless selectively allowed to escape by manual operation to deflate the balloon 306 (e.g., on removal or replacement of the drainage tube 402 in a mammalian body).

The dual channel cap 324 may, but need not necessarily include a removable plug cap 410 of the first channel 308. The plug cap 410 may be connected to an outer wall of the first channel 308 near an external drain outlet 412 of the first channel 308. Although not shown in FIG. 4 (but shown in FIG. 3), the external drain outlet 412 can include the connector 327 for coupling the external drain outlet 412 to a tube or conduit of a drainage collection bag, such as a urine collection bag.

A lateral wing 414 of the dual-channel cap 324 extends between the first channel 308 and the second channel 309 and valved external inflation conduit 310, to connect the first channel 308, second channel 309 and inflation conduit 310, in relatively fixed relation.

In operation, the anchor 312 is bonded to an external wall of a drain vessel, for example, the anchor 312 is implanted via surgical procedure to bond the anchor 312 to the bladder or to other body wall surfaces at an entry (e.g., cystostomy or other) near and adjacent to the bladder. The anchor 312 as so implanted is sandwiched and secured (such as by sutures or other bond) extra-peritoneally, between the detrusor (bladder) and adjacent to or in contact with the rectus abdominus muscles. The drainage tube 302 is thereafter inserted via surgical procedure, through a cystostymy and through the central channel 320 of the anchor 312, to extend into a drain vessel, space or reservoir, such as the bladder, at the bottom end 316. The settlement ring 304 mates with the accommodation seat 322 of the anchor 312. The inflatable balloon 306 is then inflated by fluid or gas (e.g., saline, water, air, or other liquid or gas) via the valved external inflation conduit 310, to expand against the internal balloon inflation void 608 of the anchor 312. Upon inflation of the inflatable balloon 306, the inflatable balloon 306 seals against the internal balloon inflation void 608 of the anchor 312, creating a liquid barrier for drain vessel fluids and retaining the drainage tube 302 to the anchor 312. Drain vessel fluids, for example, urine of the bladder, drain into the holes 318 and through the drainage tube 302 for exit through the first channel 308 of the dual-channel cap 324. A drain conduit 334, such as a drain conduit of a urine collection bag, may be connected to the external drain outlet 412 of the first channel 304. In embodiments including the plug cap 410, the plug cap 410 is unplugged from the external drain outlet 412 of the drainage tube 302, and the drain conduit is connected to the external drain outlet 412.

If it is desirable or becomes necessary to remove the drainage tube 302 from the drain vessel, the valve 404 of the valved external inflation conduit 310 is manually or otherwise, as applicable, triggered to open, allowing the pressurized fluid or gas within the inflatable balloon 306 to escape via the internal inflation conduit 402. A guidewire is then inserted through the drainage channel into the lumen of the cavity, space or organ, for example, the urinary bladder. Once escaped, the drainage tube 302 is manually passed from the anchor 312 and out the cystostomy leaving the guidewire in-situ. A same or different drainage tube may then be passed over the guidewire to be positioned in exactly the same location as the drainage tube 302 just removed. The new internal drainage tube is then fixed to the anchor 312 by inflation of the retention balloon within the anchors as desired and in the manner described.

Figure 6:
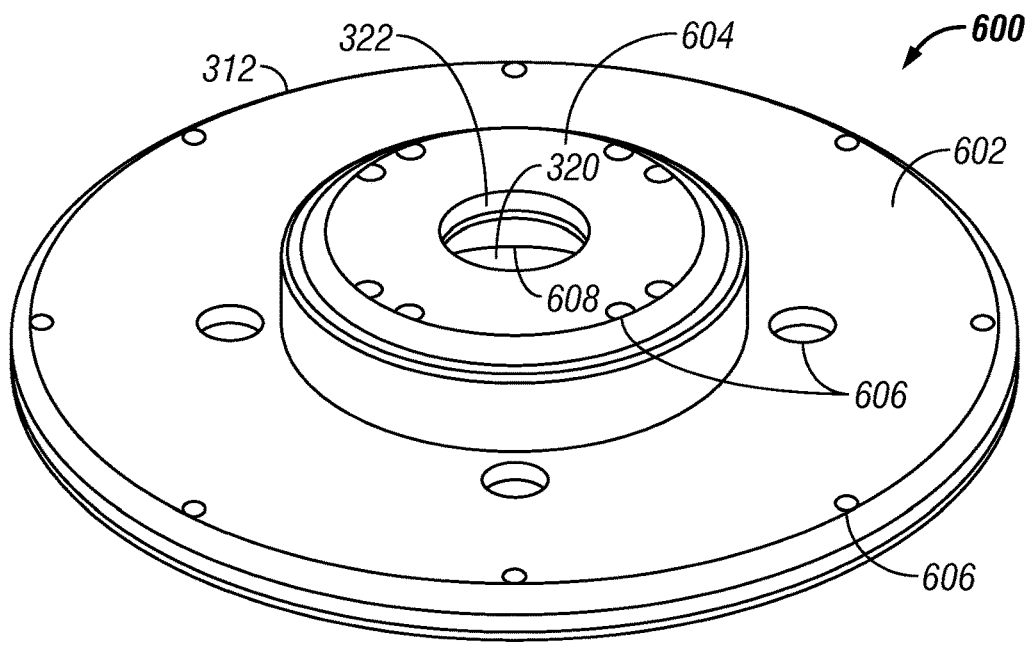
FIG. 6 illustrates a front and top perspective view of an exemplary tissue bonding anchor, according to certain embodiments of the invention.

Referring to FIG. 6, in conjunction with FIGS. 3-5, a non-exclusive embodiment 600 of the anchor 312 is a flange 602 and central cylinder 604. The flange 602 is joined with the central cylinder 604. The flange 602 includes attachment holes 604 through the thickness of the flange 602. The central cylinder 604 is hollow, forming the central channel 320 sized to accommodate the bottom end 316 of the drainage tube 302 through the central channel 320. The central channel 320 includes within the central cylinder 604 an expansive segment forming an internal balloon inflation void 608. The internal balloon inflation void 608 is sized to accommodate the inflatable balloon 306, when inflated within the bounds of the internal balloon inflation void 608, in sealed engagement with the anchor 312. The accommodation seat 322 is formed in an upper end (in the orientation of FIGS. 1 and 6) of the central channel 320. The accommodation seat 322 is sized to mate with the settlement ring 304 of the drainage tube 302 when the bottom end 316 of the drainage tube 302 is passed through the central channel 320.

Figure 7:
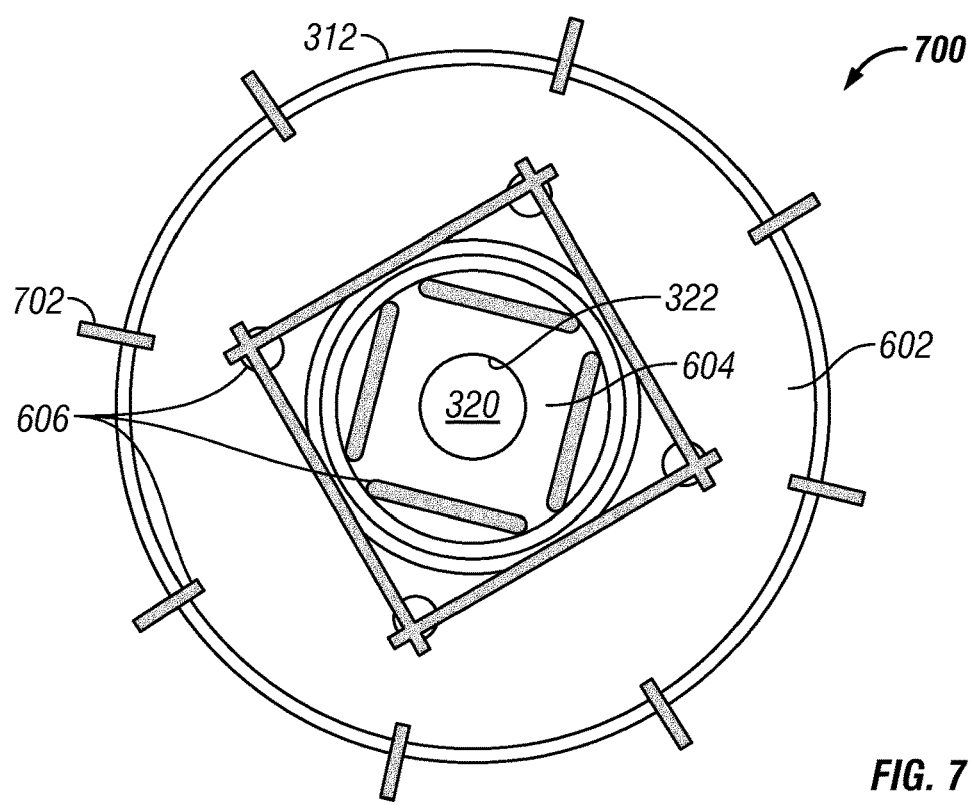
FIG. 7 illustrates a top view of the exemplary tissue bonding anchor with example sutures, according to certain embodiments of the invention.

Referring to FIG. 7, in conjunction with FIGS. 3-6, a non-exclusive embodiment of an attached anchor 700 includes attachments 702. The attachments 702 are, for example, sutures or other suitable bond connectors for fixing the anchor 312 to a drain vessel, such as the bladder. The attachments 702 pass through the attachment holes 606 of the flange 602 and the central cylinder 604, and in use, secure the anchor 312 to the drain vessel.

Figure 8:
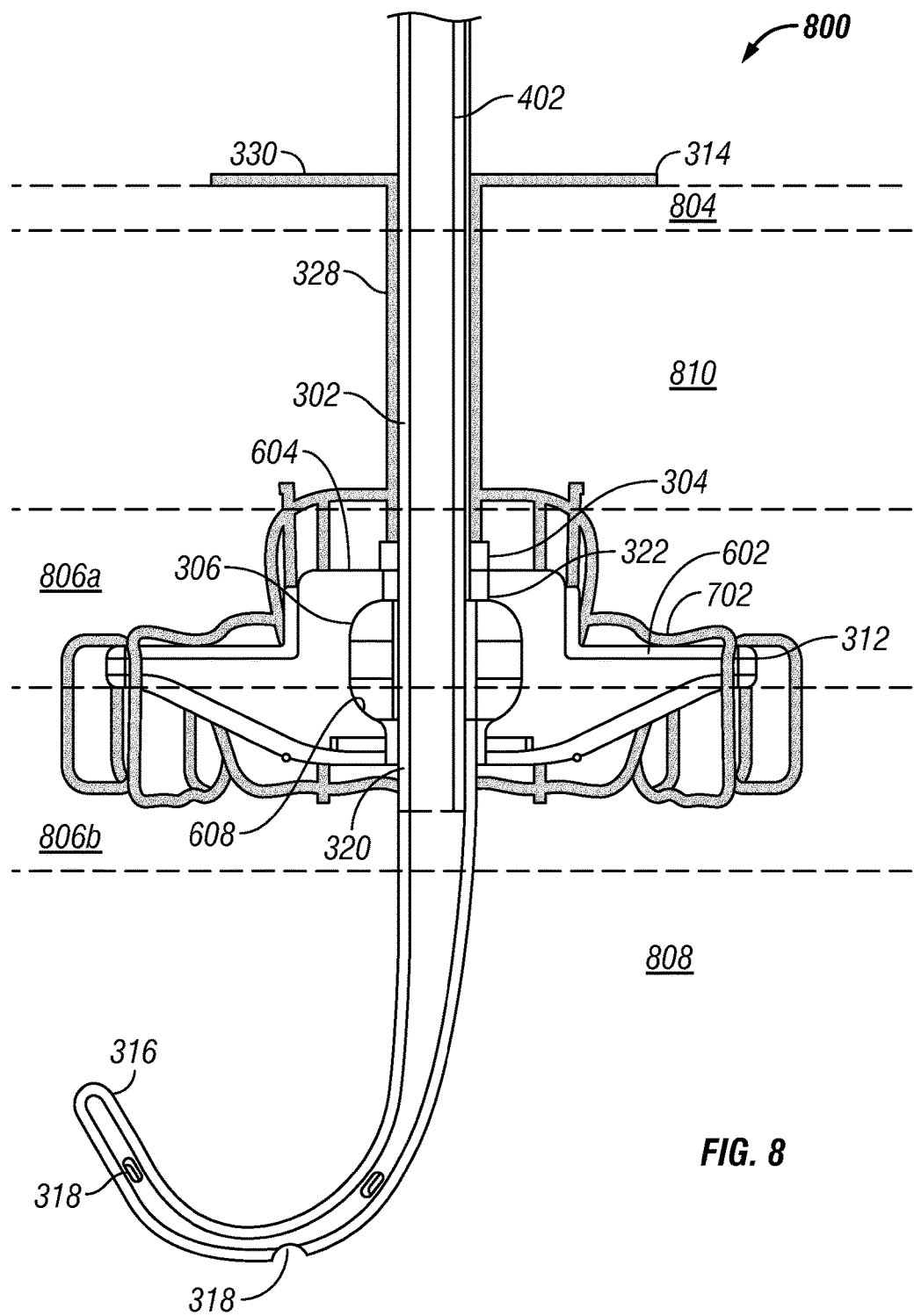
FIG. 8 illustrates a partial side view in vertical cross-section of an exemplary in use tissue bonding implantation device, according to certain embodiments of the invention.

Referring to FIG. 8, in conjunction with FIGS. 3-7, a non-exclusive embodiment of an in use tissue bonding implantation device 800, shown in vertical cross-section in FIG. 8, includes the drainage tube 302 fixed to the anchor 312 in use in a mammalian body. A cystostomy formed in the mammalian body is through the abdominal wall 804 and the bladder wall 806a and bladder lining 806b. The anchor 312 is placed in the intra-abdomen space 810 at the opening of the bladder wall 806a. The central channel 320 of the anchor 312 is aligned with the opening of the bladder 808, and the anchor 312 is attached to the bladder wall 806a by attachments 702, for example, by sutures or other suitable attachment bond device(s). The attachments 702 are passed through the bladder wall 806a and into the bladder lining 806b to secure the anchor 312.

The bottom end 316 of the drainage tube 302 is passed through the central channel 320 and into the bladder 808, until the settlement ring 304 mates with the accommodation seat 322 of the anchor 312. The inflatable balloon 306 is inflated through the internal inflation conduit 402 and expands in the internal balloon inflation void 608, to seal the drainage tube 302 to the anchor 312 (and, consequently, the bladder 808) and retain the drainage tube 302 to the anchor 312. The body may be shielded from contact with the drainage tube 302 by the transcutaneous sleeve 314. The hollow transcutaneous extension 328 of the transcutaneous sleeve 314 wraps the drainage tube 302 and is positioned within the body to the extent of the disk flange 330 of the transcutaneous sleeve 314. The transcutaneous sleeve 314 may be replaceable to avoid microbe contamination of the drainage tube 302 from the body.

Figure 9:
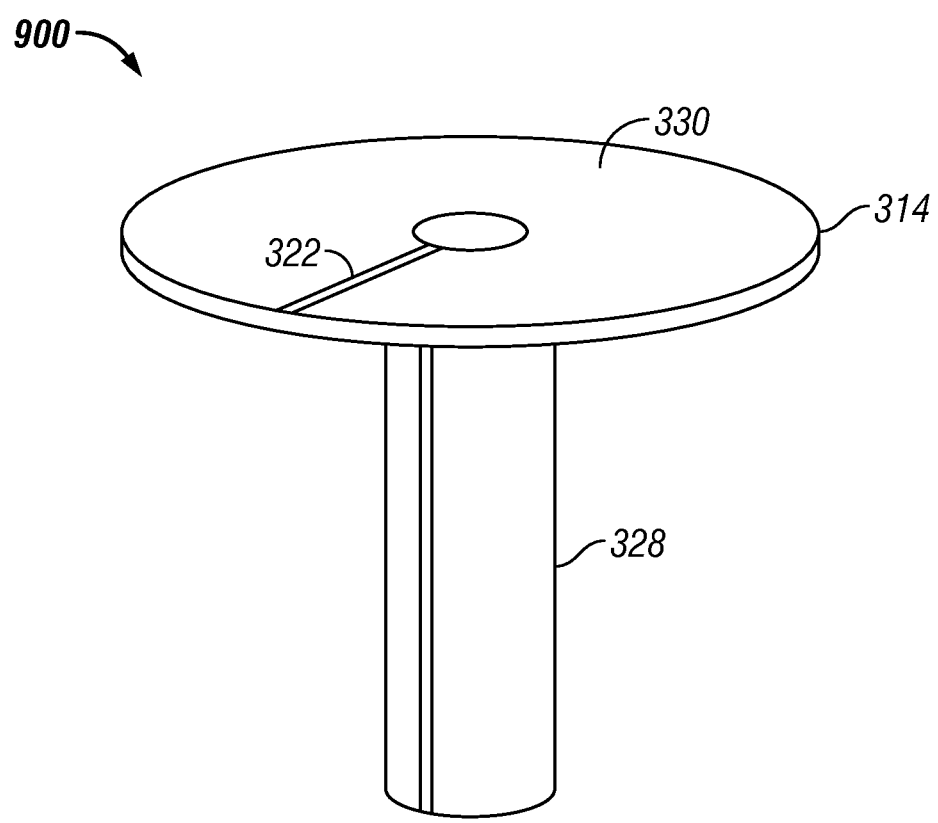
FIG. 9 illustrates a non-exclusive embodiment of the transcutaneous sleeve.

Referring to FIG. 9, in conjunction with FIGS. 3 and 8, a non-exclusive embodiment 900 of the transcutaneous sleeve 314 includes the disk flange 330 connected to the hollow transcutaneous extension 328. The disk flange 330 and the hollow transcutaneous extension 328 include a slit 322 extending radially in the disk flange 330 and connecting along length of the transcutaneous extension 328. The transcutaneous sleeve 314 is flexible (e.g., manually), separating the slit 322 sufficient to wrap the transcutaneous sleeve 314 around the drainage tube 302. The external surface of the sleeve 314 may, in certain non-exclusive embodiments, be impregnated or coated with one or multiple antimicrobial surface technologies including modulated surface patterns, modulated surface roughness and impregnated or coated molecules. Target molecules are those that block or repel microbial adhesion, microbial multiplication or replication and/or that prevent, block or disperse microbial formation of biofilms.

Figure 10:
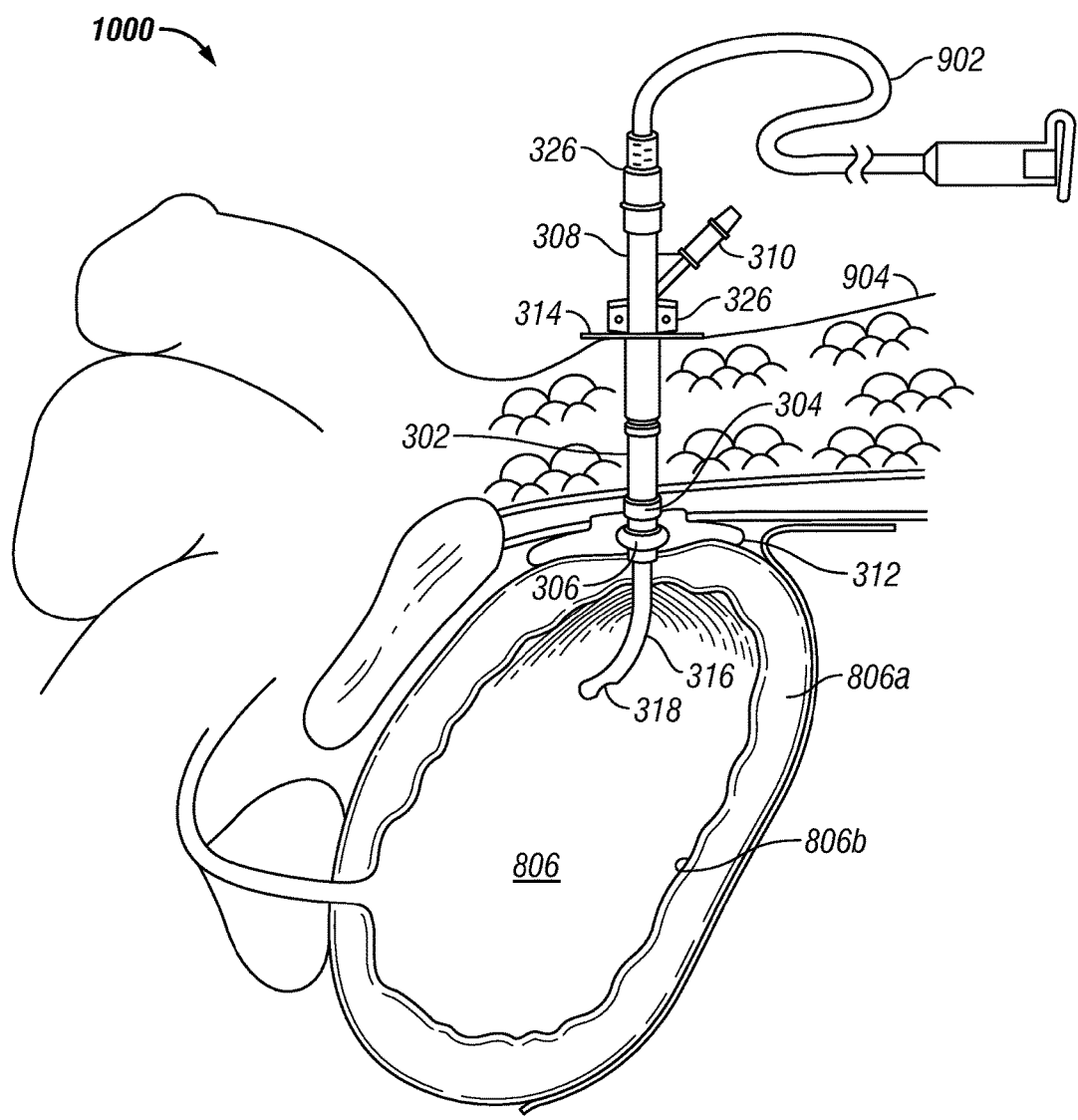
FIG. 10 illustrates a non-exclusive embodiment of the tissue bonding implantation device in use for drain of the bladder in a mammalian body shown in vertical cross-section.

Referring to FIG. 10, in conjunction with FIGS. 3-8, a non-exclusive embodiment of the tissue bonding implantation device 300 is in use for drain of the bladder 806 in a mammalian body shown in vertical cross-section. The drainage tube 302, via the connector 327 of the first channel 308 of the dual-channel cap 324 is coupled to a tube extension 902 or other conduit device. The tube extension 902 permits drain from the drainage tube 302 to selectively be capped (as shown in FIG. 10) or otherwise opened to flow to a collection bag or other disposal (not shown).

The bottom end 316 of the drainage tube 302 is retained in the bladder 806 by the seal of the inflatable balloon 306 in the anchor 312 attached to the bladder wall 806a and bladder lining 806b. The inflatable balloon 306 is inflated (or if desired deflated, for removal of the drainage tube 302 from the body) through the valved external inflation conduit 310 and internal inflation conduit 402 connected to the inflatable balloon 306. The transcutaneous sleeve 314 is placed around the drainage tube 302, such that the transcutaneous sleeve 314 remains outwardly concentric with the drainage tube 302 protruding into the cystostomy with the drainage tube 302 and the disk flange 330 resides on the skin of the body surrounding the cystostomy opening. The transcutaneous sleeve 314 shields the drainage tube 302 from microbial migration from the body. The transcutaneous sleeve 314 may be replaced, without displacement of the anchor 312 and drainage tube 302 assembly from the body.

Any suitable materials tolerable by the mammalian body or other source of drain vessel, are possible for construction of the tissue bonding implantation device. For example, the anchor 312 may be formed of a silicone cylinder-flange or as a 3 dimensional ellipsode with internal balloon chamber. The basic construct may be fabricated from any metal or synthetic polymer of which the body is tolerant, including, for example, silicone, polyurethane, poly vinyl, or other suitable materials, such as latex, silicone elastomers, or others. The top and bottom surfaces of the anchor 312 may be coated with a porous polymer, for example, PTFE, Dacron, other polyester or other substance. The drainage tube 302, as well as the settlement ring 304 and connector 327, may be formed of silicone, latex, silicone elastomers, or other suitable materials. The bottom end 316 may be tapered to aid placement in the anchor 312. The dual-channel cap 324 may similarly be formed of silicone, plastics, polyvinyl chloride (PVC), or other suitable materials. The valve may be formed of plastic, metal, silicone, latex or other suitable material, and may be selectively manually (or otherwise) activated to open and close, for example, by connection of a pressurized fluid or gas source to the external inflation conduit 310. The inflatable balloon 306 may be rubber or other suitable material formed as a toroid (or other suitable configuration), to seal the drainage tube 302 to the anchor 312. The transcutaneous sleeve 314 may be formed of silicone or other ductile material tolerable by the body. The transcutaneous sleeve 314 may be impregnated or surfaced with an antimicrobial agent, for example, an elutable, lubricious coating like that provided by polyvinyl-pyrillodine— or other known coating in the medical device industry.

In operation, the tissue bonding anchor 312 is attached through a surface, such as the skin and abdominal rectus muscles, to a reservoir, such as the bladder or other vessel. The anchor 312 is attached, for example, by sutures or other bonding device(s) that allows the anchor to implant to the vessel but be removed from attachment if necessary. The bottom end 316 of the drainage tube 302 is retained in the bladder 806 by the seal of the inflatable balloon 306 in the anchor 312 attached to the bladder wall 806a and bladder lining 806b. The inflatable balloon 306 is inflated (or if desired deflated, for removal of the drainage tube 302 from the body) through the valved external inflation conduit 310 and internal inflation conduit 402 connected to the inflatable balloon 306. The transcutaneous sleeve 314 is placed around the drainage tube 302, such that the transcutaneous sleeve 314 remains outwardly concentric with the drainage tube 302 protruding into the cystostomy with the drainage tube 302, and the disk flange 330 resides on the skin of the body surrounding the transcutaneous cystostomy opening. The transcutaneous sleeve 314 shields the drainage tube 302 from microbial migration from the skin and transcutaneous layers of the body. The transcutaneous sleeve 314 may be replaced, without displacement of the anchor 312 and drainage tube 302 assembly from the body.

Two phases of separate procedures, i.e., Phase I and Phase II, may, for example, be employed for implantation and activation of the tissue bonding device. The anchor is placed in a Phase I minor surgical procedure. Phase II, insertion and activation of the drainage tube to the anchor, may be implemented in separate procedure, for example, in the case of the bladder, Phase II may be performed about three or more months after Phase I. The three-month (or more) time interval allows fibroblastic in-growth and fixation of the anchor to the rectus and detrusor muscles. Phase II is a minor fluoroscopic-clinic procedure. In the Phase II procedure, the drainage tube is inserted over a guide wire into the bladder lumen via a small skin incision and needle puncture through the bladder wall. The drainage tube is inserted over the guide wire and locks reversibly and mechanically within the tissue-bonded anchor.

The drainage tube is therefore easily replaced, for example, monthly, by unlocking the drainage tube from the anchor through deflation of the balloon, insertion of a guide wire into the bladder lumen, removal and replacement of a new drainage tube over the guide wire, re-engagement of the locking mechanism by inflation of the balloon, and re-attachment of the external components. Drugs, e.g., antibiotics and mucosa modulating agents like Botox, can be injected directly into the bladder lumen via the self-sealing silicone injection port of the dual channel permanently attached or the separately attached cap.

If it becomes necessary, the anchor may be replaced through surgical procedure to remove the anchor from the bladder and to implant a new anchor to the bladder.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention.

Benefits, other advantages, and solutions to problems have been described above with regard to specific embodiments. However, the benefits, advantages, solutions to problems and device(s), connection(s) and element(s) that may cause any benefit, advantage, or solution to occur or become more pronounced are not to be construed as a critical, required, or essential feature or element of any or all the claims. As used herein, the terms "comprises, "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A tissue bonding implantation device, comprising:
    a drainage tube having an internal surface and an external surface;
    an inflatable balloon connected to the drainage tube, on the external surface of the drainage tube;
    a balloon inflation conduit in fluid communication with the inflatable balloon, the balloon inflation conduit extends through the drainage tube from the inflatable balloon;
    an external cap connected to the drainage tube and the balloon inflation conduit, the cap having a first sealable opening in fluid communication with the drainage tube and a second sealable opening in fluid communication with the balloon inflation conduit; and
    an anchor removably attached to the drainage tube of a central cylinder connected to a flange includes a central channel through the central cylinder and an internal balloon inflation void of the central cylinder, the inflatable balloon when lodged in the internal balloon inflation void expands via inflation through the second sealable opening of the external cap and the balloon inflation conduit to fill the internal balloon inflation void and secure the inflatable balloon to the anchor, to retain the drainage tube with the anchor.

2. The tissue bonding implantation device of claim 1, wherein inflation of the inflatable balloon of the drainage tube within the internal balloon inflation void of the anchor, reversibly and watertightly secures the drainage tube within the anchor.

3. The tissue bonding implantation device of claim 1, wherein the drainage tube is inwardly tapered along a bottom end of the drainage tube.

4. The tissue bonding implantation device of claim 1, wherein the drainage tube has side holes that allow urine to enter internal to the drainage tube along a bottom end of the drainage tube.

5. The tissue bonding implantation device of claim 4, wherein the drainage tube includes a settlement ring that seats the drainage tube in the anchor with the inflatable balloon at the internal balloon inflation void when the drainage tube is passed onto and positioned over a temporary guidewire for insertion of the drainage tube into a body and through the anchor.

6. The tissue bonding implantation device of claim 1, further comprising:
a transcutaneous sleeve having a flange extending laterally from an upper edge of a transcutaneous extension of the transcutaneous sleeve is positioned on the drainage tube with the transcutaneous extension extending into a body serviced by the drainage tube and the flange resting on skin of the body.

7. The tissue bonding implantation device of claim 6, wherein the transcutaneous sleeve is made of silicone impregnated with nitrofurazone.

8. The tissue bonding implantation device of claim 1, further comprising an external drainage tube configured to be removably connected to the external cap.

9. The tissue bonding implantation device of claim 1, wherein the second sealable opening of the external cap is made of self sealing silicone.

* * * * *